United States Patent

Jacobs et al.

[11] Patent Number: 6,165,174
[45] Date of Patent: Dec. 26, 2000

[54] INSTRUMENT FOR INTERRUPTING CONDUCTION PATHS WITHIN THE HEART

[75] Inventors: Clemens J. Jacobs, Hoevelaken; Tjong Hauw Sie, Zwolle, both of Netherlands

[73] Assignee: Clemens Josephus Jacobs, Netherlands

[21] Appl. No.: 09/180,124

[22] PCT Filed: Apr. 25, 1997

[86] PCT No.: PCT/NL97/00223

§ 371 Date: Nov. 2, 1998

§ 102(e) Date: Nov. 2, 1998

[87] PCT Pub. No.: WO97/41793

PCT Pub. Date: Nov. 13, 1997

[30] Foreign Application Priority Data

May 3, 1996 [NL] Netherlands ............................ 1003024

[51] Int. Cl.⁷ .................................................. A61B 18/18
[52] U.S. Cl. .............................................. 606/41; 607/101
[58] Field of Search ....................... 606/31, 41; 607/101, 607/102, 104, 105, 122; 600/374

[56] References Cited

U.S. PATENT DOCUMENTS

| | | |
|---|---|---|
| 4,562,838 | 1/1986 | Walker . |
| 4,920,978 | 5/1990 | Colvin . |
| 5,013,312 | 5/1991 | Parins et al. . |
| 5,167,659 | 12/1992 | Ohtomo et al. . |
| 5,246,440 | 9/1993 | Van Noord . |
| 5,277,696 | 1/1994 | Hagen . |
| 5,348,554 | 9/1994 | Imran et al. ............................ 606/41 |
| 5,431,649 | 7/1995 | Mulier et al. . |
| 5,500,012 | 3/1996 | Brucker et al. ......................... 607/122 |
| 5,522,873 | 6/1996 | Jackman et al. ........................ 607/122 |
| 5,605,539 | 2/1997 | Buelna et al. . |
| 5,643,197 | 7/1997 | Brucker et al. ............................ 604/20 |
| 5,688,267 | 11/1997 | Panescu et al. ........................... 606/41 |
| 5,785,706 | 7/1998 | Bednarek ................................. 606/41 |
| 5,823,956 | 10/1998 | Roth et al. .............................. 600/374 |
| 5,860,951 | 1/1999 | Eggers et al. ............................. 604/49 |

FOREIGN PATENT DOCUMENTS

| | | |
|---|---|---|
| 0 280 972 | 9/1988 | European Pat. Off. . |
| 0 543 123 | 5/1993 | European Pat. Off. . |
| 94 17 787 | 2/1995 | Germany . |
| WO 95/03742 | 2/1995 | WIPO . |
| WO 95/17222 | 6/1995 | WIPO . |
| WO 95/19148 | 7/1995 | WIPO . |
| WO 97/16127 | 5/1997 | WIPO . |

OTHER PUBLICATIONS

Atrial Fibrillation: Mechanisms and Therapeutic Strategies, Futura Publishing Co. Inc., Armonk, N. Y. 1994. J.L. Cox: Surgical Interruption of Atrial Reentry as a Cure for Atrial Fibrillation.

*Primary Examiner*—Michael Peffley
*Attorney, Agent, or Firm*—Quarles & Brady LLP

[57] ABSTRACT

A description is given of a probe for making stripe-shaped transmural lesions in one or more walls of the atria of the heart in open-heart surgery. The strip-shaped lesion blocks electrical impulses in a direction crosswise to the lesion. The probe has a handle (1), a closed end (2) and a relatively rigid shaft (5), and means (6, 7) for coupling the problem to an RF power source.

6 Claims, 3 Drawing Sheets

INSTRUMENT FOR INTERRUPTING CONDUCTION PATHS WITHIN THE HEART

FIELD OF THE INVENTION

The invention relates to an instrument for making at least one stripe-shaped transmural lesion in one or more walls of the atria of the heart, which lesion essentially blocks the electrical impulse conduction in a direction crosswise to the stripe-shaped transmural lesion.

BACKGROUND OF THE INVENTION

All kinds of heart arrhythmias, and in particular chronic and paroxysmal atrial fibrillation, can currently be treated by surgery.

A known surgical procedure (MAZE) was designed to eliminate atrial fibrillation permanently. In this procedure incisions are made with a scalpel in the walls of the atria, in order to block, by the thus formed interruption of the tissue continuity electrical impulse conduction in a direction crosswise to the incisions. As a result of the subsequent scarring, these electrical blocks acquire a permanent character.

This known technique is as yet performed only to a limited extent worldwide, owing to the complexity of the operation. The increased risk is particularly associated with the duration of the operation and the way in which the operation has to be carried out.

The duration of the operation, and in particular the cross-clamp time (x-clamp) is so long that there is a great risk of damage to the heart muscle.

The cross-clamp time required for the MAZE procedure alone is currently still an average of 68 min. (range 50–102 min.), and the necessary time on the heart-lung machine is on average 182 min. (range 130–256 min.). For further data you are referred to Atrial Fibrillations: Mechanisms and Therapeutic Strategies, Futura Publishing Co. Inc. Armonk, N.Y. 1994. J. L. Cox: Surgical Interruption of Atrial Reentry as a Cure for Atrial Fibrillation. The way in which the operation is performed with the scalpel produces an increased risk of vascular suture leaks and subsequent bleeding, due to the large number and location of the vascular sutures involved.

SUMMARY OF THE INVENTION

The object of the present invention is to provide an instrument of the abovementioned type which eliminates the abovementioned disadvantages, and which in particular shortens the time required for the operation and reduces the risk of bleeding and damage, therefore reducing the risk for the patient in open-heart surgery.

According to the invention, the instrument indicated is characterized in that the instrument is a probe in which the end which during the operation comes into contact with the wall to be treated is a closed electrode which can interact with an RF power source, while the probe is of a relatively rigid type.

The instrument according to the invention is a probe by means of which in open-heart surgery it is possible to make a permanent change in an atrial wall which is transmural, i.e. it extends over the entire thickness of the wall.

As will be discussed at a later stage, during the performance of the operation the electrode at the end of the probe is brought into contact with the atrial wall to be treated and is moved along it in a linear pattern. On excitation of the electrode with RF power, dielectric (RF) heating of the wall tissue occurs. The RF treatment produces a change in the cell structure of the atrial wall, with the result that electrical impulse conduction in a direction crosswise to the transmural lesion is blocked.

In order to be able to work well with it, the probe must be of a relatively rigid type, so that the electrode can be accurately positioned on and moved along the atrial wall. In the operation no disintegration of the tissue of the atrial wall occurs, and there is no risk of subsequent bleeding. The operation can be carried out on the outside or the inside of the atrium as desired.

Methods of RF heating or dielectric heating are based on the use of heat generated in materials which are relatively poor electrical conductors when they are placed in high-frequency electromagnetic fields. The heat is generated as a result of dielectric losses occurring in a material situated between metal electrodes which form a capacitor which is connected to a high-frequency (RF) generator. Such heating is highly uniform and therefore extremely suitable for use of the instrument, the probe, according to the invention. During use of the probe, one of the capacitor "plates" is formed by the electrode at the end of the probe, while the other "plate" is a counter-electrode which is stuck on, for example, the patient's back; when the latter electrode is being placed, it is preferable to use a contact gel which has electrical conductance. Of course, the counter-electrode can also be placed on the outside of the atrial wall of the heart, for example if the electrode of the probe is being brought into contact with the inside of said wall.

In connection with the invention, reference is made to WO 95/03742, which discloses a catheter comprising at the distal a metal electrode by means of which tissue erosion, also known as ablation, can be carried out.

Such a catheter typically has a length of approximately 1 meter, a diameter of approximately 2 mm, and has an electrode of approximately 2 mm diameter, and its low thickness makes it very flexible, so that it can follow a blood vessel without any problems. This catheter is suitable for local punctate ablation. Such a catheter is not suitable for use as a probe for making stripe-shaped transmural lesions in an atrial wall.

In particular, the probe according to the invention has at least a handle; an end; a relatively rigid shaft between the handle and the end, and connecting and conduction means for connecting the end of the probe to an RF power source.

In the instrument according to the invention a temperature recorder is advantageously present near the end of the probe, which temperature recorder, operating in a feedback system with the RF power source, can regulate the temperature of the end of the probe to a preset value. Through input of the RF power, the temperature of the end of the probe will generally rise; feedback with the RF power source makes it possible to ensure that the temperature of the end does not exceed a predetermined value.

With use of RF power it is extremely important that the fewest possible electrical blockages should be present in the body section between the end of the probe and the counter-electrode on the outside of the body. On account of this, it is preferable to ensure that the probe can interact with means for supplying a physiologically acceptable liquid to the end thereof. In its simplest form, such a liquid is supplied near the electrode of the probe by way of a line which does not form part of the probe. The function of the liquid is, on the one hand, to cool the electrode and, on the other, to prevent the occurrence of electrically insulating air gaps which adversely affect the efficiency of the RF action.

It is very advantageous for the probe according to the invention itself to have means for discharging a physiologically acceptable liquid near the end of the probe. Said liquid will generally preferably have a certain degree of electrical conduction, and is expediently a physiological salt solution.

In a very attractive embodiment, the instrument has between the handle of the probe and the shaft inlet means for introducing the physiologically acceptable liquid, which inside the shaft remains electrically insulated from the connecting and conduction means present in the shaft, while near the end it has outflow means for the physiologically acceptable liquid. With this embodiment, the functioning of the probe can be improved yet further, and it can be ensured that the greatest RF energy effect is concentrated in the wall of the atrium to be treated, forming the desired transmural lesion.

At the side of the handle facing away from the end of the probe, the conduction and connecting means of the probe according to the invention comprise a connector connected thereto, with contact means for connection of the electrode to the end of the probe and the temperature recorder present therein to the RF power source.

The connector is preferably of the rapid coupling type, so that easy coupling to the RF power source is permitted.

In order to make handling of the instrument according to the invention, in the form of a probe, as easy as possible for the operating surgeon during an open-heart operation, the shaft of the probe preferably has an intrinsic curvature, which is expediently approximately 140°.

BRIEF DESCRIPTION OF THE DRAWINGS

The invention will now be explained with reference to the drawing, in which.

DETAILED DESCRIPTION OF THE DRAWINGS

Figure 1:
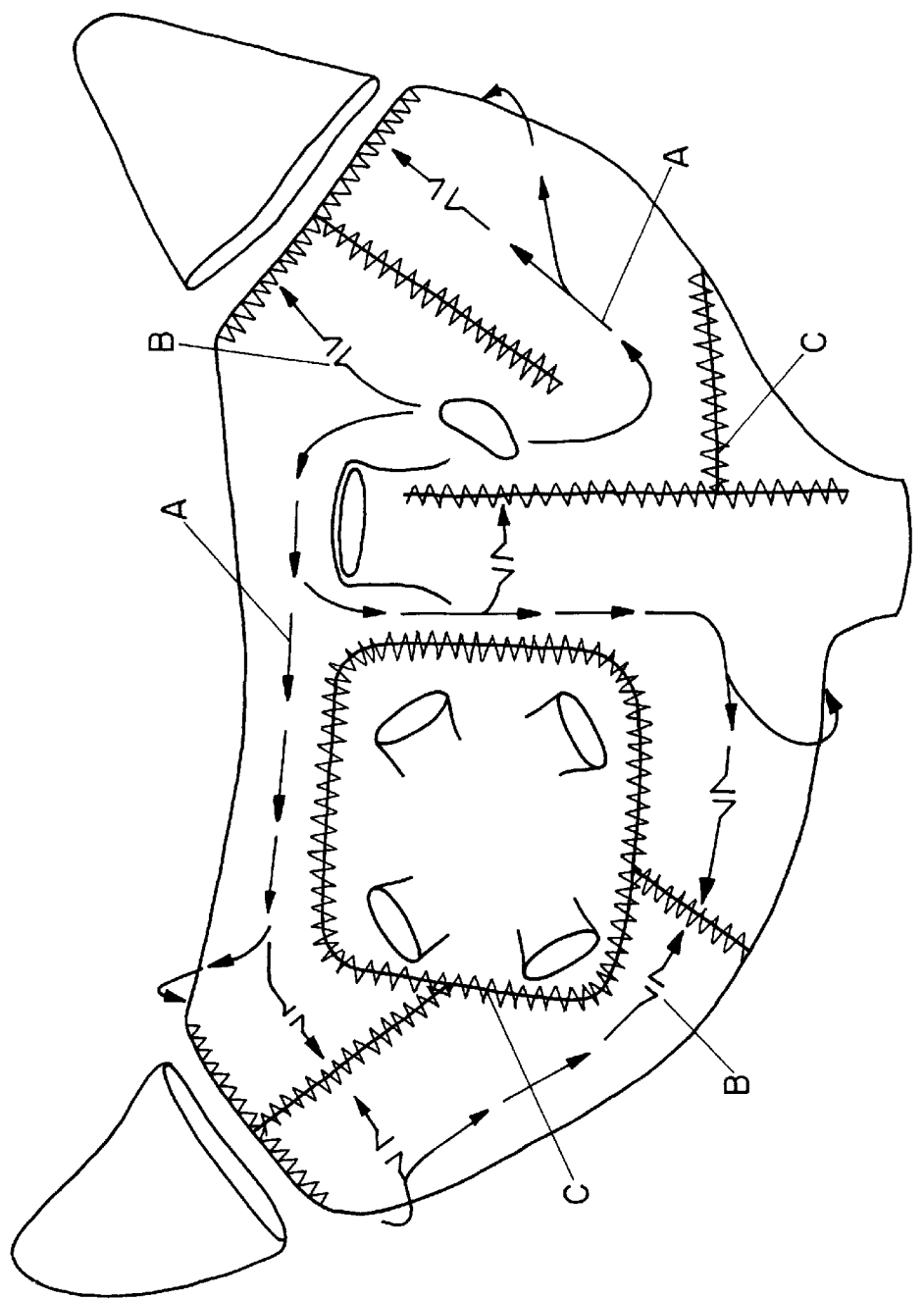
FIG. 1 shows a schematic picture of the transmural lesions which can be made with the instrument according to the invention, and which can block electrical impulses in directions crosswise to said lesions.

FIG. 1 shows diagrammatically in a two-dimensional view the two atria of a human heart, in which the transmural lesions are indicated by reference letter C, the undisturbed electrical impulses by A, and the blocked electrical impulses by B. The lesions C are in the nature of scar tissue which is formed after treatment using the probe according to the invention.

Figure 2:
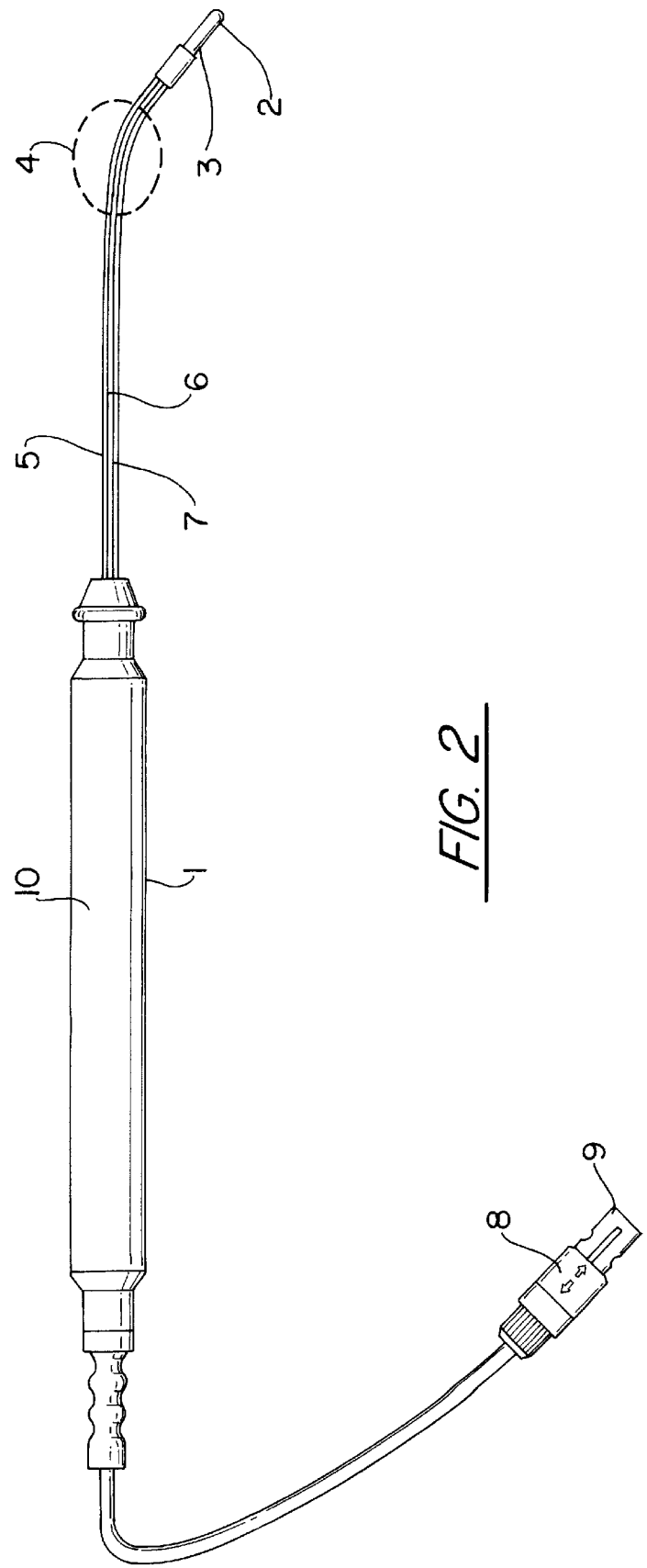
FIG. 2 shows an instrument according to the invention in a first embodiment.

FIG. 2 shows a probe according to the invention in a first embodiment, and shows a handle 1, an active metal end 2 as a closed electrode with indication of the position of a temperature sensor 3. The shaft of the probe 5 has a curvature 4 of approximately 140°, and inside the shaft run the electrical wires 6 for exciting the closed electrode-type end 2 and wire 7 for connecting the temperature sensor which is fitted at the position of reference number 3.

Inside the handle 1 are electrical switch means 10 (not shown in any further detail) for permitting connection of the probe to the RF generator (not shown). Reference numbers 8 and 9 also indicate a connector making it possible to couple the probe to the RF generator.

Figure 3:
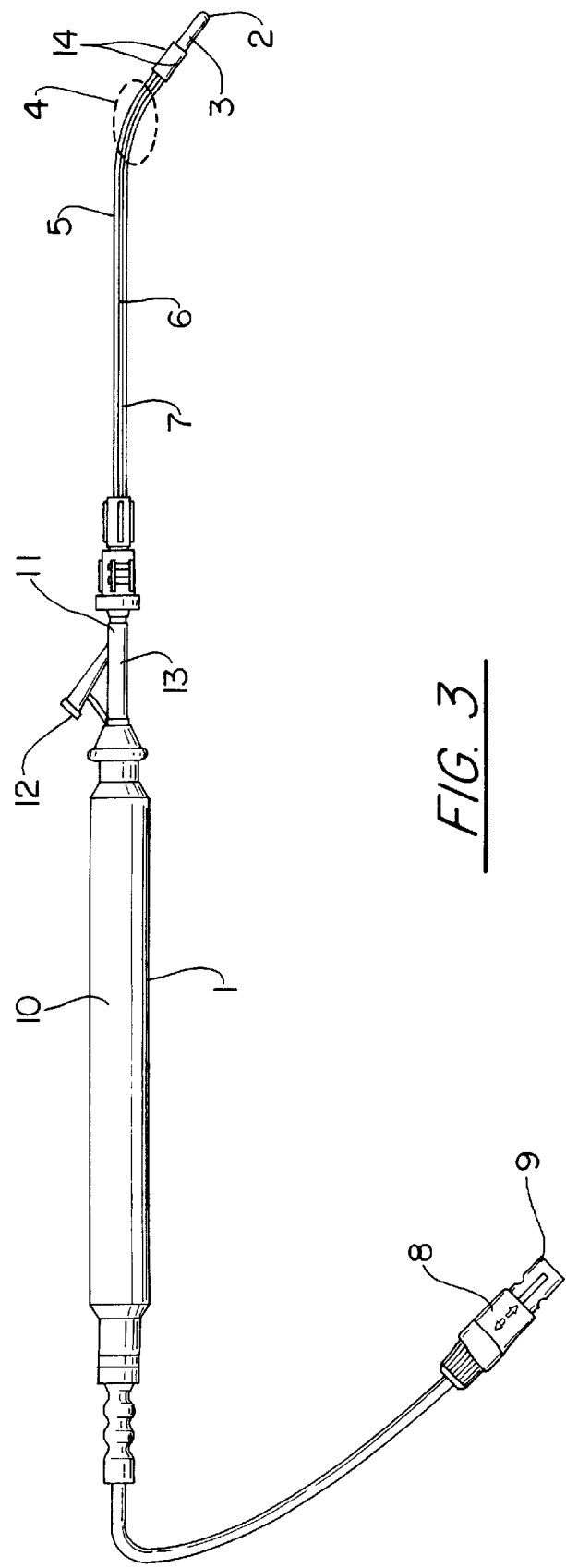
FIG. 3 shows an instrument according to the invention in a second embodiment.

FIG. 3 shows a particularly advantageous embodiment of the probe according to the invention, which is identical to the probe of FIG. 2, but in which reference number 11 indicates a Y-connector which makes it possible to supply a physiologically acceptable liquid by way of a port 12 into the shaft 5, said physiologically acceptable liquid being guided through the shaft 5 without contact with the conduction means 6 and 7. The physiologically acceptable solution flows by way of the port 12 to an inner shaft 13, and from there by way of the shaft 5 to the outflow ports 14 which are disposed in the vicinity of the metal end 2. The physiologically acceptable liquid is expediently a physiological salt solution which is readily tolerated by the body.

The physiological salt solution, on the one hand, achieves cooling of the closed electrode 2 and, on the other hand, lowers the electrical resistance between the closed electrode of the end 2 and the atrial wall. Extremely good and reproducible results are obtained with the probe shown in the figure. The source of RF power is typically a generator which can deliver a power of, for example, maximum 50 watt at a frequency of 500 kHz. The power supplied is a function of the temperature set and the tissue contact of the electrode forming the end of the probe. The desired temperature can be set at the generator, and in general lies in the range 50 to 70° C. If temperatures higher than the given range are permitted, burning of the tissue (coagulation) will occur, with the result that an insulating layer is formed; said layer will make further action of the RF energy difficult, with the result that underlying tissue is not treated fully, if at all.

The end 2 of the probe expediently comprises platinum and is typically a cylindrical shape with a diameter of 4 mm. The diameter can generally lie between 3 and 6 mm.

The total length of the probe without connection means is typically approximately 35 cm, the handle being approximately 20 cm long, the shaft approximately 10 cm, and the end approximately 2 cm. In general, the length of the shaft 5 lies between 8 and 15 cm, and the shaft has a diameter between 3 and 6 mm and is made of a physiologically acceptable plastic. Suitable plastics are nylon 66, polypropylene and high-density polyethylene.

What is claimed is:

1. An instrument for supplying RF energy to body tissue, said instrument comprising a probe having:

a handle;

a closed electrode at one end of the probe, the instrument being adapted to allow the electrode to be accurately positioned on and moved along an atrium wall during open heart surgery and to make at least one stripe-shaped transmural conduction blocking lesion in said atrium wall;

a connection and conduction means electrically communicating with the electrode and adapted for connecting the electrode to an RF power source;

a shaft connecting the handle and the electrode, the shaft being more rigid than a catheter which is adapted for following a blood vessel;

a temperature recorder at the end of the probe with the electrode, the temperature recorder being adapted to operatively communicate with a feedback system and the RF power source such that the temperature of the electrode can be regulated to a preset value; and means for supplying a physiologically acceptable liquid to the electrode, the means for supplying the liquid being connected to the shaft, wherein the probe is sufficiently rigid such that an operator grasping the handle of said instrument can accurately position and move the electrode along an atrium wall to be treated such that the instrument can be used in an open-heart operation to make at least one stripe-shaped transmural conduction blocking lesion in said atrium wall.

2. The instrument of claim 1, wherein the shaft has an intrinsic curvature.

3. The instrument of claim 2, wherein the curvature is approximately 140 degrees.

4. The instrument of claim 1, wherein the length of the shaft lies between 8 and 15 cm; the shaft has a diameter between 3 and 6 mm and is made of a physiologically acceptable plastic.

5. The instrument of claim 2, wherein the length of the shaft lies between 8 and 15 cm; the shaft has a diameter between 3 and 6 mm and is made of a physiologically acceptable plastic.

6. The instrument of claim 3, wherein the length of the shaft lies between 8 and 15 cm; the shaft has a diameter between 3 and 6 mm and is made of a physiologically acceptable plastic.

* * * * *